(12) United States Patent
Furudate

(10) Patent No.: US 8,340,375 B2
(45) Date of Patent: Dec. 25, 2012

(54) MEDICAL DIAGNOSTIC IMAGING APPARATUS, MEDICAL IMAGE PROCESSING METHOD, AND COMPUTER PROGRAM PRODUCT

(75) Inventor: Naoyuki Furudate, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 1081 days.

(21) Appl. No.: 12/010,677

(22) Filed: Jan. 29, 2008

(65) Prior Publication Data

US 2008/0188735 A1    Aug. 7, 2008

(30) Foreign Application Priority Data

Feb. 2, 2007   (JP) ................................. 2007-024231
Nov. 21, 2007  (JP) ................................. 2007-301630

(51) Int. Cl.
*G06K 9/00* (2006.01)

(52) U.S. Cl. ........ 382/128; 382/130; 382/131; 382/132; 128/920; 128/922; 128/923

(58) Field of Classification Search .................. 382/128, 382/130, 131, 132; 128/920, 922, 923
See application file for complete search history.

(56) References Cited

U.S. PATENT DOCUMENTS

2002/0090058 A1 * 7/2002 Yasuda et al. ................. 378/205

FOREIGN PATENT DOCUMENTS

| JP | 2001/22964   | 1/2001  |
|----|--------------|---------|
| JP | 2002/360564  | 12/2002 |
| JP | 2003-210430  | 7/2003  |
| JP | 2007/130240  | 5/2007  |
| JP | 2007-167634 A| 7/2007  |
| WO | 01/03065     | 1/2001  |

OTHER PUBLICATIONS

Office Action in JP 2007-301630 issued Sep. 18, 2012 with English translation.

* cited by examiner

*Primary Examiner* — David A Vanore
*Assistant Examiner* — Nicole Ippolito
(74) *Attorney, Agent, or Firm* — Nixon & Vanderhye PC

(57) ABSTRACT

An operator designates a reference plane on a medical image or a region of a patient, and a setting unit specifies whether the reference plane is an axial plane, a sagittal plane, or a coronal plane. The setting unit also specifies vertical, horizontal, and anteroposterior directions on the reference plane based on an anatomical characteristic of the region. Information about relationship between a patient coordinate system and a region coordinate system is stored in association with the medical image in a first storage unit.

17 Claims, 9 Drawing Sheets

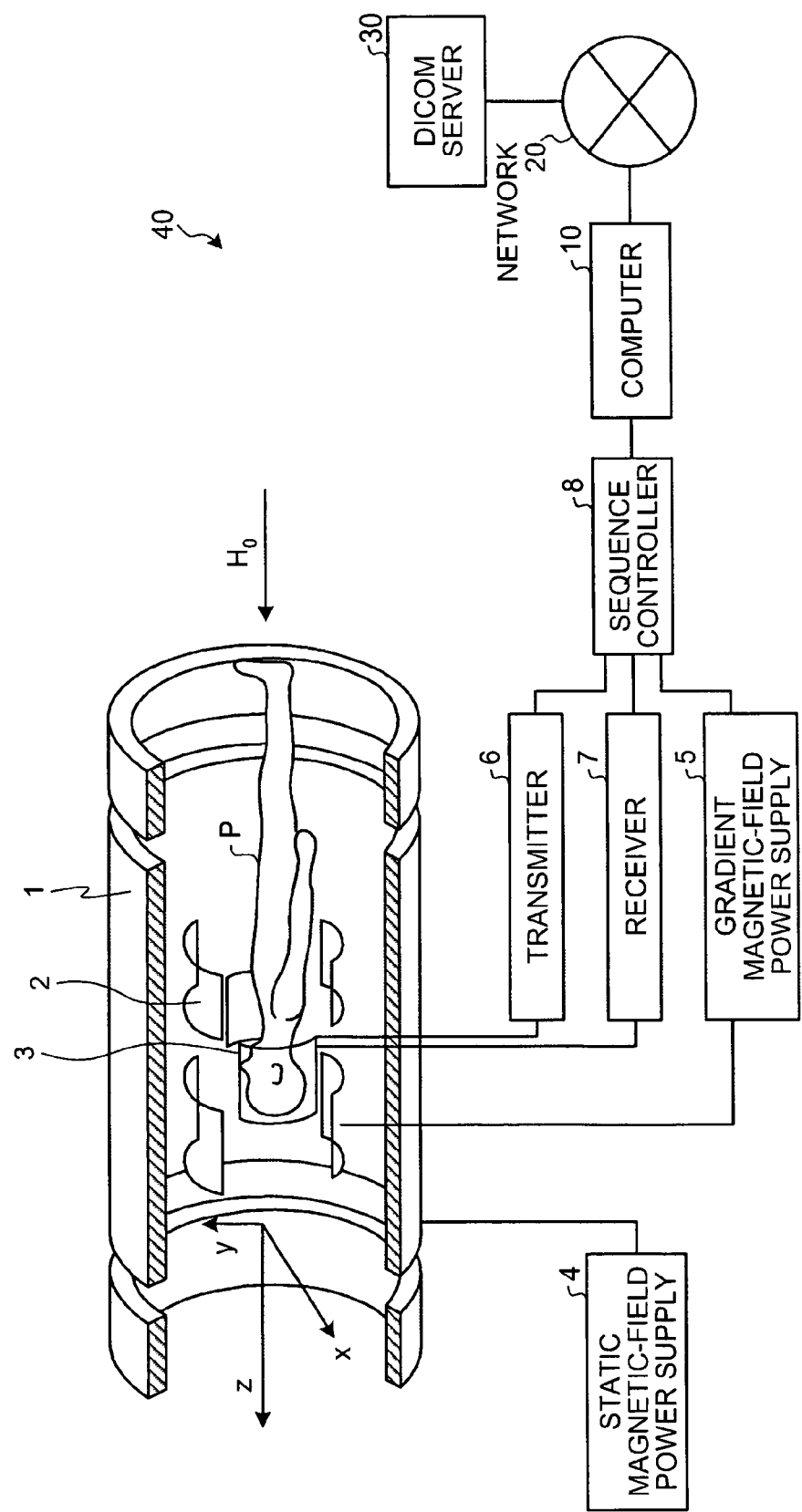

FIG.5
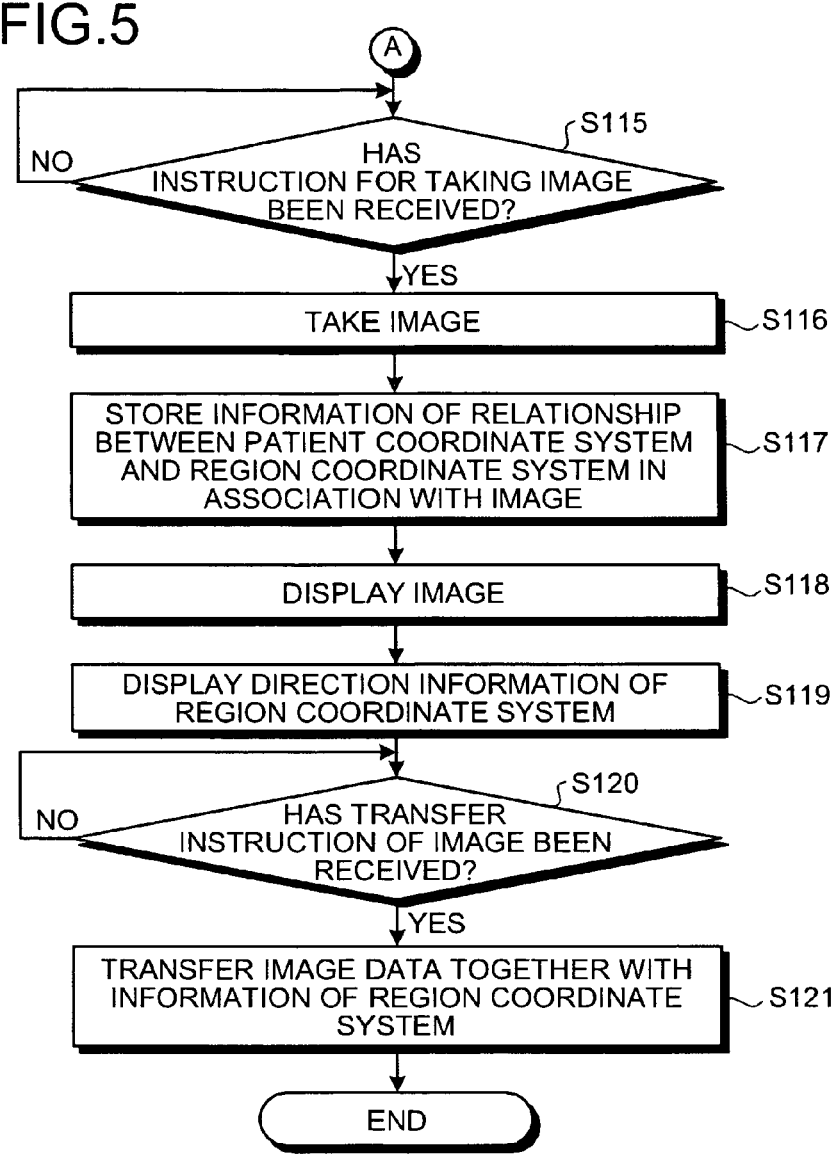
FIG.6A
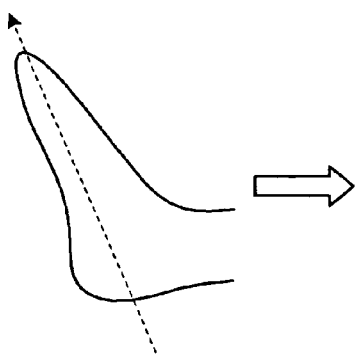
FIG.6B
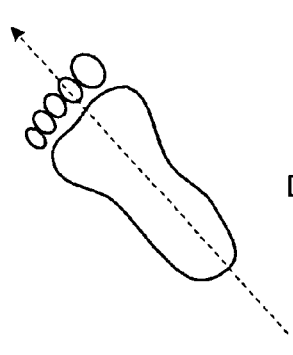
FIG.6C
REFERENCE PLANE A FIG.10A   FIG.10B   FIG.10C   FIG.10D
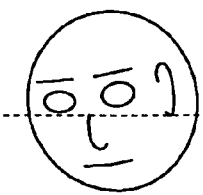 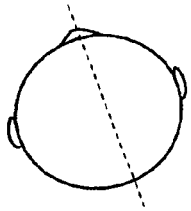 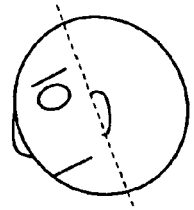 
TAKE CO IMAGE IN CONCERNED REGION BY SEQUENTIALLY
APPLYING OBLIQUE PROCESS
FIG.10E   FIG.10F   FIG.10G
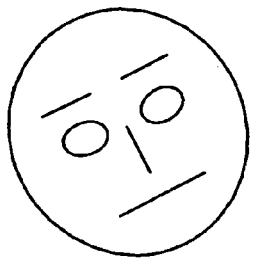 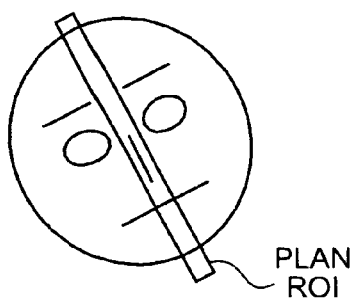 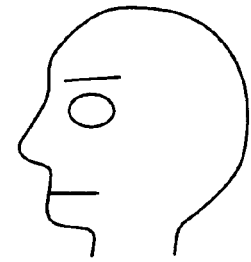
PLAN ROI
SPECIFY CO AS REFERENCE PLANE A
SPECIFY REFERENCE PLANE B ON REFERENCE PLANE A
SPECIFY SG AS REFERENCE PLANE B

MEDICAL DIAGNOSTIC IMAGING APPARATUS, MEDICAL IMAGE PROCESSING METHOD, AND COMPUTER PROGRAM PRODUCT

CROSS-REFERENCE TO RELATED APPLICATIONS

This application is based upon and claims the benefit of priority from the prior Japanese Patent Application No. 2007-24231, filed on Feb. 2, 2007 and the prior Japanese Patent Application No. 2007-301630, filed on Nov. 21, 2007; the entire contents of which are incorporated herein by reference.

BACKGROUND

1. Technical Field

The exemplary embodiment relates to a medical diagnostic imaging apparatus, a medical image processing method, and a computer program product.

2. Description of the Related Art

Recently, with advancement of scanning techniques and image processing techniques, it has become possible to take images of various regions of a patient (an object), at various positions and from various angles, with medical diagnostic imaging apparatuses such as magnetic resonance imaging (MRI) apparatuses and computed tomography (CT) apparatuses. For example, JP-A 2003-210430 (KOKAI) describes a technique for easily taking sectional images of a centrum, such as vertebra and lumbar vertebra, taking images of which has been heretofore considered to be difficult due to a three-dimensionally curved shape.

In such medical diagnostic imaging apparatuses, a coordinate system having three directions, that is, vertical, horizontal, and anteroposterior, centering on the apparatus, is defined to indicate a position and an angle for using the apparatus. Such a coordinate system is specific to the apparatus for which it is defined, so that it is referred to as an "apparatus coordinate system". However, because the patient is scanned in various postures and directions, a coordinate system, which is separate from the apparatus coordinate system, that is based on the posture and the direction of the patient is preferable. Therefore, a variable coordinate system determined by the posture of the patient (supine position (face up), prone position (face down), right decubitus position, and left decubitus position) and an insertion direction into the apparatus (from head, from feet) is defined. Because the variable coordinate system is uniquely determined based on the posture of the patient at the time of scanning, such is referred to as a "patient coordinate system".

Depending on the type of medical test, a plurality of regions needs to be diagnosed with respect to one patient, and an image of each region is required. However, if each region is imaged separately, the total time required for scanning increases, and a burden on the patient to be scanned becomes large. Therefore, a plurality of regions is generally scanned at one stretch by setting a wider range for scanning to shorten the time. In this case, the directions of the regions in the taken image are indicated based on the same patient coordinate system.

At the time of diagnosing each region, however, if the direction of the region projected on the image is indicated based on the patient coordinate system, interpretation of radiogram becomes difficult. Normally, when each region is diagnosed, visual inspection is performed from multilateral directions on the basis of directions (vertical, horizontal, or anteroposterior directions) specifically determined for each region from an anatomical point of view. The direction, which becomes a basis, does not always agree with the direction indicated by the patient coordinate system.

This problem is particularly noticeable, for example, when a patient who cannot lie down with his body, upper limbs (arms), and lower limbs (legs) being stretched is scanned, or when scanning is performed with a region, which tends to be inclined in various directions with respect to a body axis even in the natural posture, such as legs, being included in the scanning range.

Thus, there has been a need of a medical diagnostic imaging apparatus, a medical image processing method, and a computer program product that can display an image together with the directions specifically determined for each region from an anatomical point of view.

SUMMARY

According to one aspect of an exemplary embodiment, there is provided a medical diagnostic imaging apparatus that includes a first storage unit that stores therein a medical image of an object; and a second storage unit that stores therein information about relationship between a first coordinate system and a second coordinate system in association with the medical image, the first coordinate system corresponding to a posture of the object at a time of taking of the medical image, and the second coordinate system being different from the first coordinate system.

According to another aspect of an exemplary embodiment, there is provided a medical image processing method including storing in a first storage unit a medical image of an object; and storing in a second storage unit information about relationship between a first coordinate system and a second coordinate system in association with the medical image, the first coordinate system corresponding to a posture of the object at a time of taking of the medical image, and the second coordinate system being different from the first coordinate system.

According to still another aspect of an exemplary embodiment, there is provided a computer program product that causes a computer to perform the above method.

BRIEF DESCRIPTION OF THE DRAWINGS

FIG. 2 is a schematic diagram for explaining a configuration of an MRI apparatus according to the first embodiment;

FIG. 5 is a continuation of the flowchart shown in FIG. 4;

FIGS. 6A to 6C are schematic diagrams for explaining an operation for specifying a reference plane;

FIGS. 10A to 10G are schematic diagrams for explaining an operation for setting a type of a reference plane.

DETAILED DESCRIPTION OF EXEMPLARY EMBODIMENTS

Exemplary embodiments will be explained below in detail with reference to the accompanying drawings. The exemplary embodiments have been explained below by using an MRI apparatus as an example. A direction specifically determined for each region from an anatomical point of view is referred to as "anatomical direction" in the explanation below.

Figure 1A:
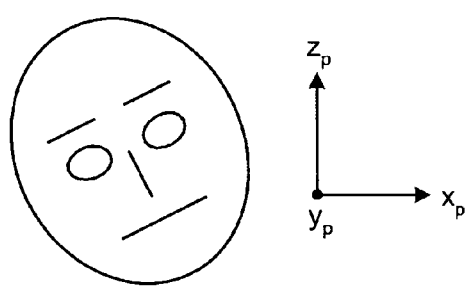
FIGS. 1A to 1F are schematic diagrams for explaining a concept of a region-coordinate system according to a first embodiment of the present invention.
Figure 1B:
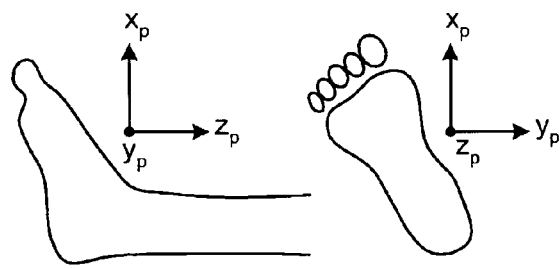
Figure 1C:
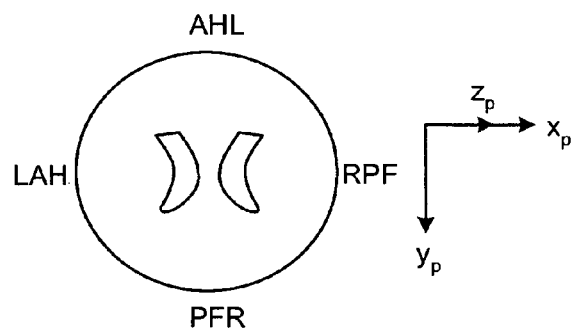
Figure 1D:
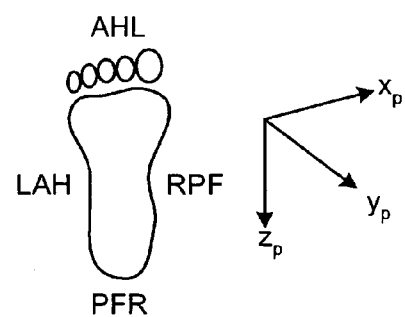

A concept of setting of a region-coordinate system in an MRI apparatus according to a first embodiment of an exemplary embodiment is explained first. FIGS. 1A to 1F are schematic diagrams for explaining this concept. FIGS. 1A to 1D respectively depict images of body parts of a patient in a patient ($x_p$, $y_p$, $z_p$) coordinate system. Specifically, FIG. 1A depicts an image of a front of the head, FIG. 1B depicts an image of a side of a foot and front of the foot, FIG. 1C depicts a sectional image of the head, and FIG. 1D depicts a sectional view of the foot.

"AHL", "LAH", "PFR", and "RPF" in FIGS. 1C and 1D respectively represent direction information determined based on the direction in the patient coordinate system. When it is assumed that a character indicating a horizontal direction is R/L (right/left), a character indicating a vertical direction is H/F (head/feet), and a character indicating an anteroposterior direction is A/P (anterior/posterior), vertical, horizontal, or anteroposterior inclinations of the sectional image are expressed by combining these characters.

In the image in which a direction is indicated based on the patient coordinate system, because a region is expressed as being inclined in a plurality of directions, it cannot be intuitively determined how much the region is inclined to the anatomical direction.

In the MRI apparatus according to the first embodiment, a coordinate system for indicating directions specifically determined for each region-anatomically is set, separately from the apparatus coordinate system and the patient coordinate system. Such a coordinate system is hereinafter referred to as a "region coordinate system".

In the first embodiment, one image specified by an operator from the sectional images obtained by scanning an object is registered as a reference plane, the type of the reference plane of the reference image is determined from among an axial plane, a sagittal plane, and a coronal plane, and an appropriate region coordinate system specific to the region is set based on the reference plane of the reference image.

Figure 1E:
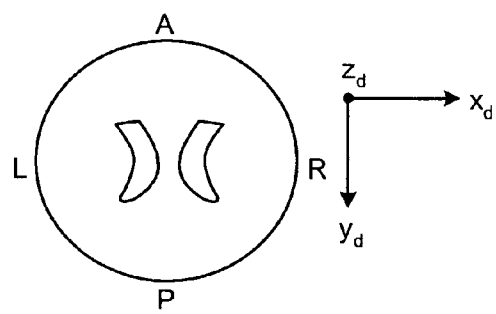
Figure 1F:
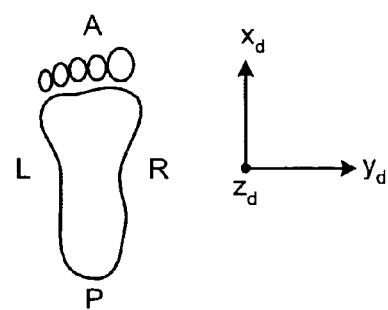

FIGS. 1E and 1F depict images of a body part of a patient in a patient ($X_d$, $y_d$, $z_d$) coordinate system. In the example shown in FIG. 1E, the sectional image shown in FIG. 1C is taken as a reference image, and a reference plane of the reference image is taken as an axial plane. On the other hand, in the example shown in FIG. 1F, the sectional image shown in FIG. 1D is taken as a reference image, and a reference plane of the reference image is taken as an axial plane.

In this manner, in the region coordinate system, because a direction is expressed by one character in the image of the reference plane, the sectional image can be intuitively determined as the sectional image as seen from one direction (in this example, vertical direction) of the three directions (vertical, horizontal, and anteroposterior directions) included in an anatomical direction.

Thus, in the MRI apparatus according to the first embodiment it becomes possible to display an image together with the directions specifically determined for each region based on the anatomical angle.

FIG. 2 is a schematic diagram for explaining a configuration of the MRI apparatus 40 according to the first embodiment. The MRI apparatus 40 includes a static magnetic-field magnet 1, a gradient magnetic-field coil 2, a radio frequency (RF) coil 3, a static magnetic-field power supply 4, a gradient magnetic-field power supply 5, a transmitter 6, a receiver 7, a sequence controller 8, and a computer 10.

The static magnetic-field magnet 1 is a cylindrically formed magnet, and generates static magnetic field $H_0$ in a space in the cylinder, in which an object P is placed, by current supplied from the static magnetic-field power supply 4. The gradient magnetic-field coil 2 includes three pairs of coils arranged inside of the static magnetic-field magnet 1. The gradient magnetic-field coil 2 generates a gradient magnetic field along three directions of x, y, and z inside the static magnetic-field magnet 1 by the current supplied from the gradient magnetic-field power supply 5.

The RF coil 3 is arranged opposite to the object P in an opening of the static magnetic-field magnet 1. The RF coil 3 irradiates RF waves transmitted from the transmitter 6 to the object P, and receives an MR signal discharged from a hydrogen nucleus of the object P due to excitation. The static magnetic-field power supply 4 supplies the current to the static magnetic-field magnet 1, and the gradient magnetic-field power supply 5 supplies the current to the gradient magnetic-field coil 2 based on an instruction from the sequence controller 8.

The transmitter 6 transmits the RF waves to the RF coil 3 based on the instruction from the sequence controller 8. The receiver 7 detects the MR signal received by the RF coil 3, and digitalizes the MR signal to generate raw data. Upon completion of generation of the raw data from the MR signal, the receiver 7 transmits the generated raw data to the sequence controller 8.

The sequence controller 8 performs scanning of the object P by driving the gradient magnetic-field power supply 5, the transmitter 6, and the receiver 7 based on sequence information transmitted from the computer 10. The sequence information defines a procedure at the time of scanning, such as the strength of the power to be supplied from the gradient magnetic-field power supply 5 to the gradient magnetic-field coil 2 and timing for supplying the power, the strength of the RF signal transmitted from the transmitter 6 to the RF coil 3 and timing for transmitting the RF signal, and timing for detecting the RF signal by the receiver 7.

When the raw data is transmitted from the transmitter 6 as a result of scanning the object P, the sequence controller 8 transfers the raw data to the computer 10.

The computer 10 controls the MRI apparatus 40 based on an instruction from the operator, and reconstructs the image from the raw data to be transmitted from the sequence controller 8. The computer 10 is connected to a digital imaging and communication in medicine (DICOM) server 30 via a network 20. The DICOM server 30 stores the image reconstructed by the computer 10.

Figure 3:
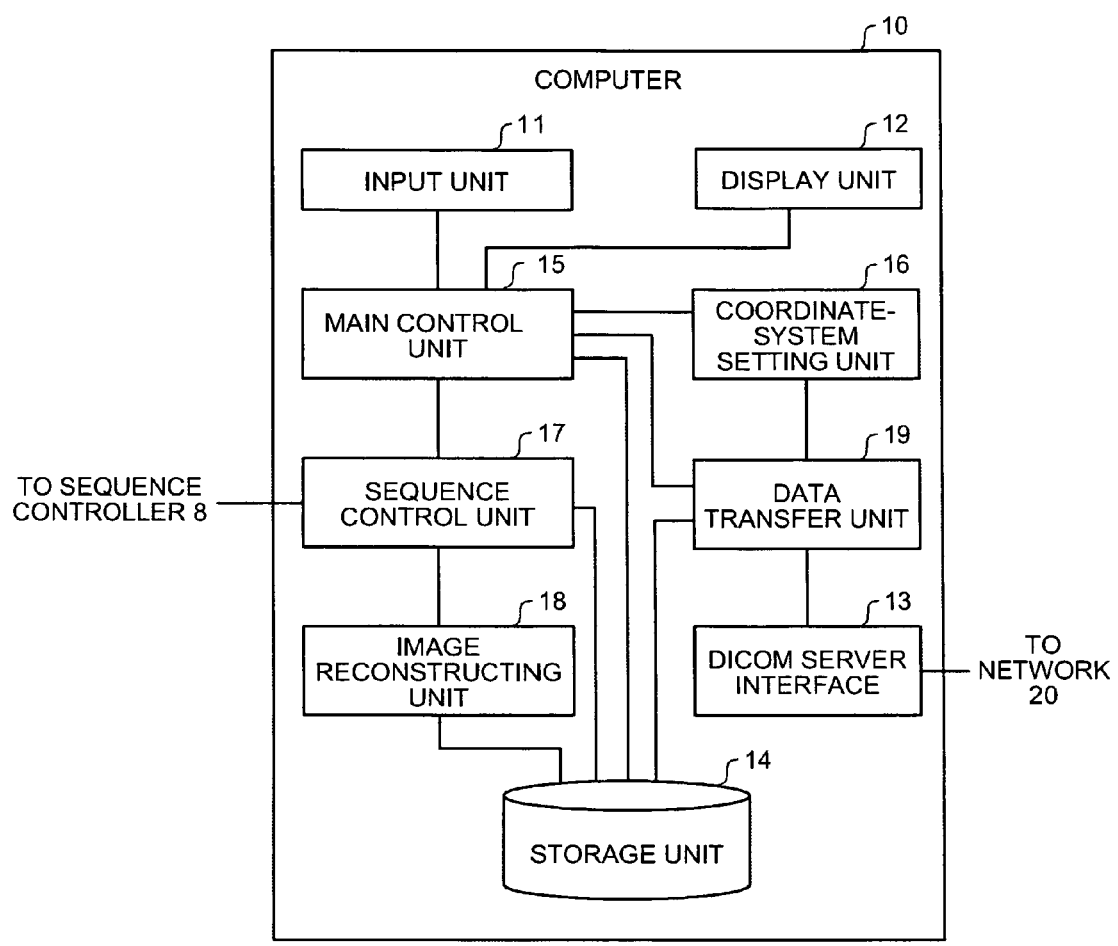
FIG. 3 is a functional block diagram of a configuration of a computer shown in FIG. 2.

FIG. 3 is a functional block diagram of the computer 10. The computer 10 includes an input unit 11, a display unit 12, a DICOM server interface 13, a storage unit 14, a main control unit 15, a coordinate-system setting unit 16, a sequence control unit 17, an image reconstructing unit 18, and a data transfer unit 19. The functional blocks shown in FIG. 3 can be realized as hardware, software, or both.

The input unit 11 is operated by the operator for inputting various pieces of information, and it is realized by a pointing device such as a mouse, a trackball, a keyboard, or a combination of these. The input unit 11 provides a user interface for receiving various instructions to the operator in cooperation with a display unit 12. For example, by operating the input unit 11 the operator can input instruction related to scanning, scanning conditions, and the like.

The display unit 12 displays various pieces of information for the operator to see, and it is realized by a cathode ray tube (CRT) display, a liquid crystal display, or the like. For example, the display unit 12 displays the image or the like reconstructed by the image reconstructing unit 18.

The DICOM server interface 13 controls transfer of data between the DICOM server 30 and the DICOM server interface 13 via the network 20. For example, the DICOM server interface 13 transmits the data or the like reconstructed by the image reconstructing unit 18 to the DICOM server 30.

The storage unit 14 stores therein data or computer programs required for various types of processing performed by the computer 10. For example, the storage unit 14 stores raw data transmitted from the sequence controller 8 and the image (medical image) reconstructed by the image reconstructing unit 18.

The main control unit 15 controls the MRI apparatus 40 by controlling the operation of respective functional units based on an instruction from the operator. For example, when the main control unit 15 receives an instruction to take an image input by the operator via the input unit 11, the main control unit 15 generates the sequence information in which a procedure at the time of scanning is defined, and transmits the generated sequence information to the sequence control unit 17. Accordingly, the sequence controller 8 takes the image in response to the instruction of the operator. When the sequence control unit 17 takes the image, the main control unit 15 reads an image reconstructed by the image reconstructing unit 18 from the storage unit 14 after scanning, and displays the image on the display unit 12.

The main control unit 15 controls the coordinate-system setting unit 16 based on the instruction from the operator to set the region coordinate system based on the anatomical characteristic of the region of the object, for the image stored in the storage unit 14. The process procedure for setting the region coordinate system will be explained later in detail.

After the coordinate-system setting unit 16 has set the region coordinate system, when the image of the object is taken, the main control unit 15 generates information of relationship between the patient coordinate system and the region coordinate system based on the posture of the object at the time of scanning, and stores the generated information in association with the image stored in the storage unit 14. The information of the relationship between the reference coordinate system and the region coordinate system herein indicates the relative positions of the both coordinate systems, and for example, the information is expressed by a rotation angle and a shift amount based on either one of the coordinate systems.

When storing the information of the relationship between the patient coordinate system and the region coordinate system, the main control unit 15 stores the information of respective coordinate systems in association with the image. The information of the coordinate system includes a direction of the image displayed based on the coordinate system, and is expressed, for example, by a vector.

The main control unit 15 reads the reconstructed image from the storage unit 14 to display the image on the display unit 12, and generates direction information indicating the vertical, horizontal, and anteroposterior directions based on the information of the region coordinate system associated with the image, to display the direction information together with the image. Accordingly, at the time of reading the image, the interpreter can easily ascertain the direction of the region.

The main control unit 15 can be configured to display the direction information based on the information of the region coordinate system. Alternatively, the main control unit 15 can be configured to select which of the patient coordinate system and the region coordinate system is to be used to display the direction information based on the instruction from the operator, to make the display unit 12 display the direction information. In the later configuration, the operator can appropriately select the direction of the image suitable for diagnosis.

The coordinate-system setting unit 16 sets the region coordinate system based on the instruction from the main control unit 15. Specifically, the coordinate-system setting unit 16 designates a sectional image of a region specified by the operator based on an anatomical view as the reference plane, specifies the type of the reference plane as any one of the axial plane, the sagittal plane, and the coronal plane, and specifies the vertical, horizontal, and anteroposterior directions in the sectional image of the region on the reference plane, thereby setting the region coordinate system based on the specified type of the reference plane and the specified respective directions in the reference plane. The process procedure for setting the region coordinate system will be explained later in detail.

The sequence control unit 17 controls transfer of data between the sequence controller 8 and the sequence control unit 17. For example, the sequence control unit 17 transmits the sequence information received from the main control unit 15 to the sequence controller 8. On the other hand, the sequence control unit 17 receives raw data from the sequence controller 8 and stores the received raw data in the storage unit 14.

The image reconstructing unit 18 reconstructs the image from the raw data. Specifically, the image reconstructing unit 18 reads the raw data stored in the storage unit 14 based on the instruction from the main control unit 15, and performs predetermined image reconstructing processing such as Fourier transform with respect to the read raw data, thereby reconstructing the two-dimensional or three-dimensional image. The image reconstructing unit 18 stores the reconstructed image in the storage unit 14.

The data transfer unit 19 transmits the image stored in the storage unit 14 (image reconstructed by the image reconstructing unit 18) to the DICOM server 30 via the DICOM server interface 13.

Figure 4:
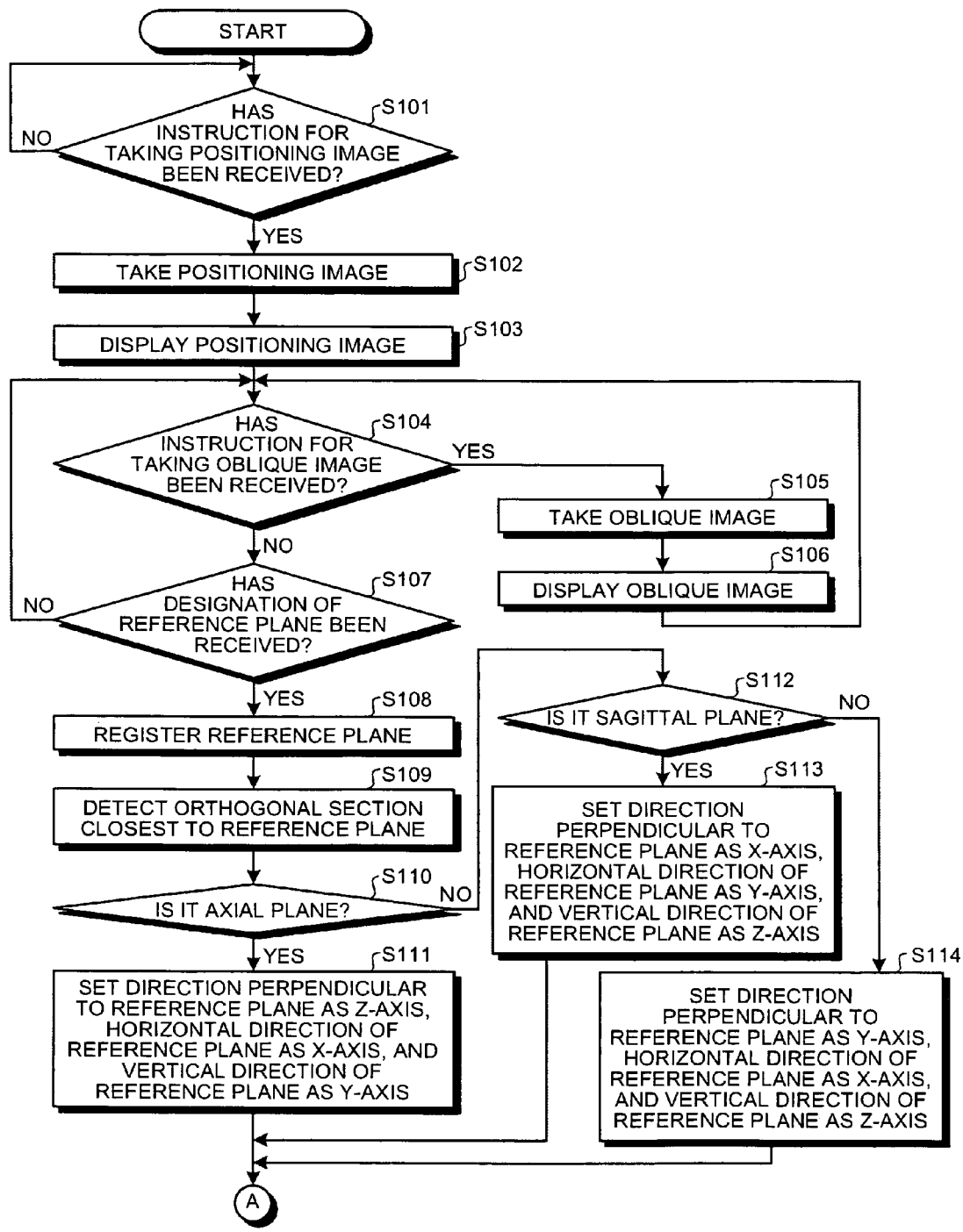
FIG. 4 is a flowchart of a process for setting a region-coordinate system according to the first embodiment.

FIGS. 4 and 5 are flowcharts of the process for setting the region-coordinate system setting in the MRI apparatus 40. The process performed by the computer 10 is mainly explained here.

As shown in FIG. 4, when the main control unit 15 receives an instruction for taking a positioning image via the input unit 11 (YES at step S101), the computer 10 takes the positioning image based on specified scanning condition (step S102). The "positioning image" is an image that is used to prepare a scanning plan for scanning the object.

An image taking process is specifically explained. The main control unit 15 first generates the sequence information based on the specified scanning condition and transmits the generated sequence information to the sequence controller 8. Accordingly, the sequence controller 8 performs scanning. The sequence control unit 17 stores the raw data received from the sequence controller 8 in the storage unit 14. The image reconstructing unit 18 reads the raw data from the storage unit 14, reconstructs a positioning image from the raw data, and stores the positioning image in the storage unit 14.

The main control unit 15 reads the positioning image from the storage unit 14 and displays the image on the display unit 12 (step S103).

Thereafter, when an instruction for taking an oblique image (image obtained by scanning an oblique section) with respect to the positioning image is received via the input unit 11 (YES at step S104), the main control unit 15 takes an oblique image (step S105), and displays the taken oblique image on the display unit 12 (step S106). The main control unit 15 repeatedly performs scanning and display of oblique images if a plurality of instruction for taking oblique images is received successively.

On the other hand, when a designation of the reference plane is received via the input unit 11 (YES at step S107), the main control unit 15 instructs the coordinate-system setting unit 16 to register the sectional image (the positioning image or the oblique image) displayed on the display unit 12 at that time as the reference plane (step S108).

An operation for specifying the reference plane is explained with reference to FIGS. 6A to 6C. An operation of the MRI apparatus 40 is explained here, adopting the operator's point of view. FIGS. 6A, 6B, and 6C depict an image obtained by taking a foot of the object. For example, when a sectional image shown in FIG. 6A is assumed to be the positioning image, the operator specifies a slice plane orthogonal to the foot with respect to the positioning image. It is assumed here that the sectional image shown in FIG. 6B is taken as the oblique image according to this operation.

The operator can further specify a slice plane orthogonal to the foot with respect to the oblique image. The operator finds a sectional image of the region orthogonal to any one of the directions anatomically determined for the foot based on the anatomical view, by repeating taking of the oblique image. The operator designates the found sectional image as the reference plane (see FIG. 6C).

Returning to FIG. 4, the coordinate-system setting unit 16 detects an orthogonal section positioned closest to the designated reference plane, that is, the orthogonal section having the smallest crossing angle from the cross sections (axial plane, sagittal plane, and coronal plane) orthogonal to the coordinate axis defined in the patient coordinate system (step S109).

When the detected plane is the axial plane (YES at step S110), the coordinate-system setting unit 16 sets the direction perpendicular to the reference plane as z-axis, the horizontal direction of the reference plane as x-axis, and the vertical direction of the reference plane as y-axis (step S111). When the detected plane is the sagittal plane (YES at step S112), the coordinate-system setting unit 16 sets the direction perpendicular to the reference plane as x-axis, horizontal direction of the reference plane as y-axis, and vertical direction of the reference plane as z-axis (step S113).

Further, when the detected plane is neither the axial plane nor the sagittal plane (i.e., when the detected plane is the coronal plane) (NO at step S112), the coordinate-system setting unit 16 sets the direction perpendicular to the reference plane as y-axis, the horizontal direction of the reference plane as x-axis, and the vertical direction of the reference plane as z-axis (step S114). The coordinate-system setting unit 16 arranges the set x-axis, y-axis, and z-axis to be orthogonal to each other at the center of the reference plane, thereby setting the region coordinate system.

The coordinate-system setting unit 16 detects the orthogonal section (axial plane, sagittal plane, and coronal plane) in the patient coordinate system closest to the reference plane set based on the operator's anatomical view, and sets the region coordinate system based on the detected section. Accordingly, the operator can set the region coordinate system, which is anatomically specific to each region, by simple operation.

Continuing to the flowchart shown in FIG. 5, when an instruction for taking an image is received via the input unit 11 (YES at step S115), the main control unit 15 performs taking of the image in the same manner as the positioning image described above (step S116). The main control unit 15 stores in the storage unit 14 the information of the relationship between the patient coordinate system and the region coordinate system and the information of the respective coordinate systems, in association with the image (step S117).

Subsequently, the main control unit 15 displays the taken image on the display unit 12 (step S118), and also displays the direction information based on the information of the region coordinate system associated with the image (step S119).

When an instruction for transferring the image is received via the input unit 11 (YES at step S120), the main control unit 15 instructs the data transfer unit 19 to transfer the image data of the image.

The data transfer unit 19 having received the instruction reads out the image data of the instructed image from the storage unit 14, and transmits the read image data to the DICOM server 30 via the DICOM server interface 13, together with the information of the region coordinate system associated with the image (step S121).

Because the data transfer unit 19 transfers the image stored in the storage unit 14 to the DICOM server 30 together with the information of the region coordinate system associated with the image, the DICOM server 30 can display the image, together with the directions specifically determined for each region based on the anatomical point of view.

In the first embodiment, because the coordinate system specific to each region is set based on the anatomical characteristic of the region of the object, an image can be displayed together with the direction specifically determined for each region based on the anatomical point of view.

In the first embodiment, the main control unit 15 receives designation of the reference plane obtained by taking the section of the region of the object from the operator via the input unit 11, and the coordinate-system setting unit 16 specifies the type of the sectional image of the region on the reference plane as any one of the axial plane, the sagittal plane, and the coronal plane. The coordinate-system setting unit 16 also specifies the vertical, horizontal, and anteroposterior directions in the reference plane, to set the region coordinate system based on the specified type of the reference plane and the specified respective directions in the reference plane. Accordingly, an image can be displayed, together with the directions specifically determined for each region based on the operator's anatomical point of view.

In the first embodiment, a case that the type of the reference plane is specified by detecting the plane closest to the designated reference plane from the sections (axial plane, sagittal plane, and coronal plane) orthogonal to the coordinate axis defined by the patient coordinate system, when the operator designates the reference plane, and the region coordinate system is automatically set based on the type of the specified reference plane has been explained. However, the present invention is not limited thereto. For example, the operator can make various determinations required until the region coordinate system is set, such as specification of the type of the reference plane. Accordingly, the region coordinate system can be flexibly set in response to a request of the operator.

A case that the operator can not only select the reference plane but also specify the type of the reference plane and input the direction of the coordinate axis and the like is explained as a second embodiment of the present invention. The configuration of the MRI apparatus 50 according to the second embodiment is the same as that according to the first embodiment. The difference lies in the processing performed by the main control unit 15 and the coordinate-system setting unit 16 in the computer 10.

Figure 7:
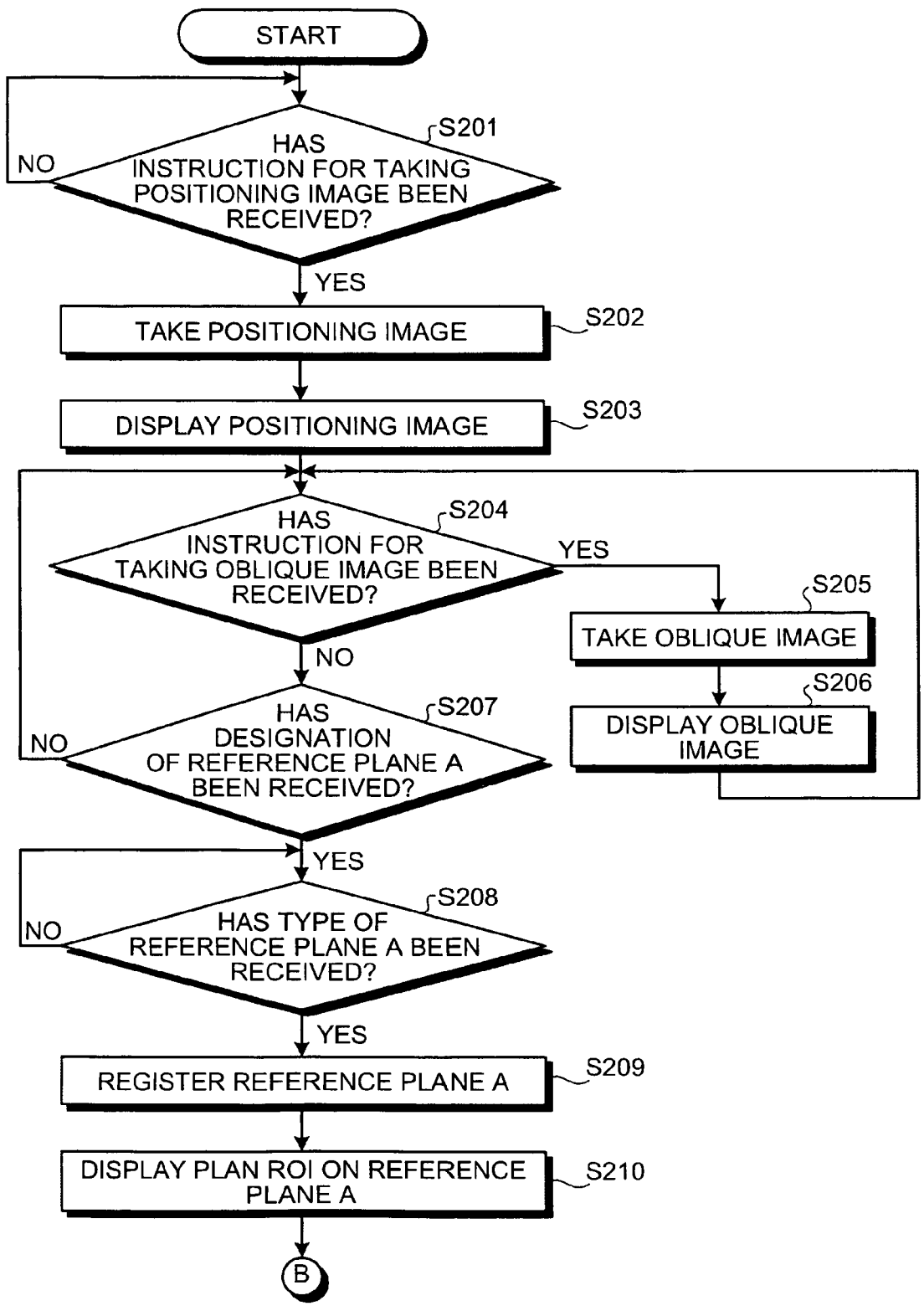
FIG. 7 is a flowchart a process for setting a region-coordinate system setting according to a second embodiment of the present invention.
Figure 8:
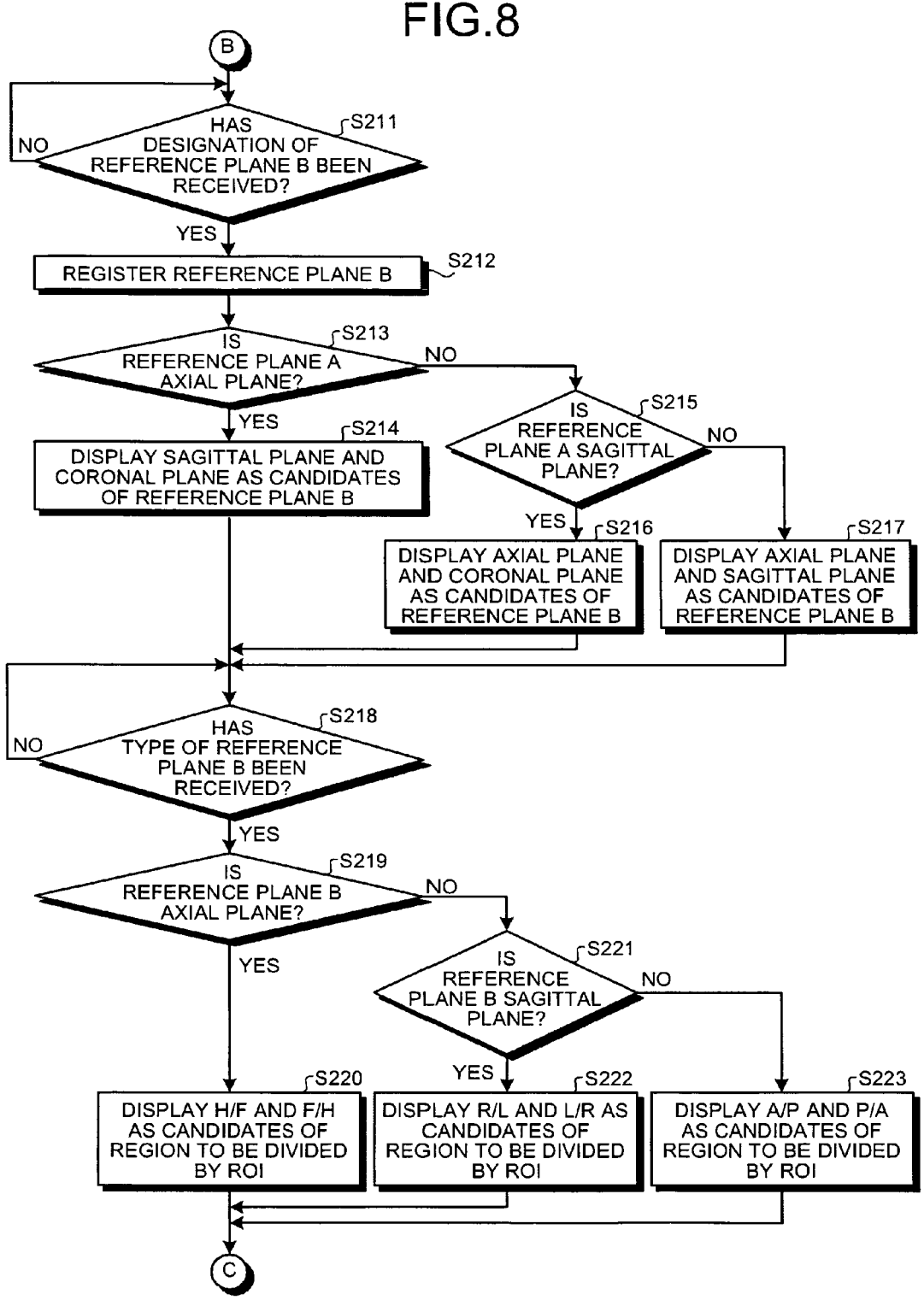
FIG. 8 is a continuation of the flowchart shown in FIG. 7.
Figure 9:
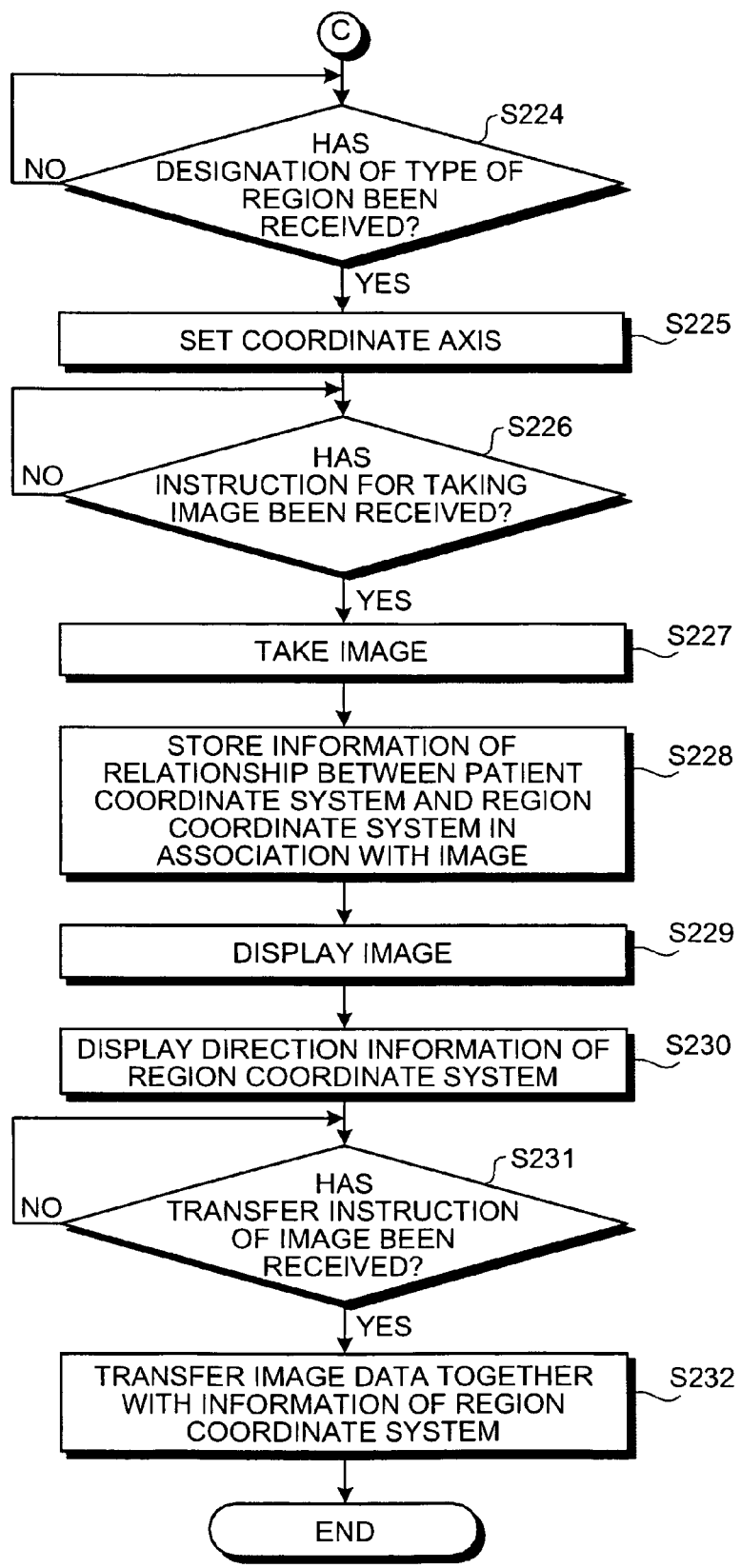
FIG. 9 is a continuation of the flowchart shown in FIG. 8.

FIGS. 7, 8, and 9 are flowcharts of a process for setting a region-coordinate system according to the second embodiment. The process performed by the computer 10 shown in FIG. 3 is mainly explained as in the first embodiment, and explanations of the same process as that explained with reference to FIGS. 4 and 5 will be omitted.

The process from step S201 to step S207 shown in FIG. 7 is the same as the process from step S101 to step S107 shown in FIG. 4, and therefore explanations thereof will be omitted. The reference plane specified by the operator is referred to as a reference plane A.

When a designation of the reference plane A is received via the input unit 11 (YES at step S207), the main control unit 15 waits until the type of the reference plane A is designated. When the designation of the type of the reference plane A is received (YES at step S208), the main control unit 15 instructs the coordinate-system setting unit 16 to register the sectional image (positioning image or oblique image) displayed on the display unit 12 at that point in time as the reference plane A (step S209).

The coordinate-system setting unit 16 having been instructed to register the reference plane A instructs the main control unit 15 to display a plan region of interest (ROI) on an image of the reference plane A displayed on the display unit 12. The plan ROI here is a region expressing a rectangular area, which is used by the operator to specify the position of a reference plane B (sectional image) orthogonal to the reference plane A, with respect to the reference plane A.

Upon reception of the display instruction of the plan ROI, the main control unit 15 displays the plan ROI on the reference plane A displayed on the display unit 12 (step S210), and waits for designation of the position of the reference plane B.

As shown in FIG. 8, when the designation of the position of the reference plane B is received via the input unit 11 (YES at step S211), the main control unit 15 instructs the coordinate-system setting unit 16 to register the sectional image at the designated position as the reference plane B (step S212).

The coordinate-system setting unit 16 having been instructed to register the reference plane B requests the operator to specify the type of the reference plane B. At this time, the coordinate-system setting unit 16 narrows down candidates of the reference plane B according to the already specified type of the reference plane A to display the candidates on the display unit 12.

Specifically, when the reference plane A is the axial plane (YES at step S213), the coordinate-system setting unit 16 instructs the main control unit 15 to display the sagittal plane and the coronal plane as the candidates of the reference plane B (step S214).

When the reference plane A is not the axial plane (NO at step S213), but the sagittal plane (YES at step S215), the coordinate-system setting unit 16 instructs the main control unit 15 to display the axial plane and the coronal plane as the candidates of the reference plane B (step S216).

Further, when the detected plane is neither the axial plane nor the sagittal plane (i.e., when the plane is the coronal plane) (NO at step S215), the coordinate-system setting unit 16 instructs the main control unit 15 to display the axial plane and the sagittal plane as the candidates of the reference plane B (step S217).

Upon receiving the type of the reference plane B selected from the displayed candidates via the input unit 11 (YES at step S218), the main control unit 15 notifies the coordinate-system setting unit 16 of the received type of the reference plane B.

Thus, the main control unit 15 displays the two remaining types of the sectional image, excluding the type of the sectional image specified as the type of the reference plane A from the axial plane, the sagittal plane, and the coronal plane. When either one of the displayed two types of the sectional image is selected by the operator, the coordinate-system setting unit 16 specifies the selected type of the sectional image as the type of the reference plane B, thereby enabling to facilitate the operation of the operator.

The operation until the type of the reference plane B is specified is explained with reference to FIGS. 10A to 10G. The operation of the MRI apparatus 50 is explained here, adopting the operator's point of view. FIGS. 10A to 10G respectively depict an image obtained by scanning the head of the object. For example, when it is assumed that the sectional image shown in FIG. 10A is the positioning image, the operator specifies a slice plane orthogonal to the head with respect to the positioning image. It is assumed here that the sectional image shown in FIG. 10B is taken as the oblique image by this operation.

The operator further specifies a slice plane orthogonal to the head with respect to the oblique image. By repeating the operation, the operator finds a sectional image of the region orthogonal to any one of the anatomical directions, and specifies the found sectional image as the reference plane A (see FIGS. 10C and 10D).

Further, the operator further specifies the type of the reference plane A. For example, it is assumed that the operator specifies the coronal plane (CO) as the type of the reference plane A (see FIG. 10E). At this stage, the MRI apparatus 50 displays the plan ROI on the reference plane A.

The operator specifies a scanning position of the reference plane B by rotating the plan ROI (see FIG. 10F). At this time, the MRI apparatus 50 displays the candidates of the type of the reference plane B. For example, when it is assumed that the operator specifies the coronal plane as the reference plane A, the axial plane (AX) and the sagittal plane (SG) are displayed as the candidates of the type of the reference plane B. The operator selects, for example, the sagittal plane from the displayed candidates (see FIG. 10G).

Returning to FIG. 8, when the type of the reference plane B is notified, the coordinate-system setting unit 16 asks the operator to specify the type (head/foot or foot/head, left/right or right/left, anterior/posterior or posterior/anterior) of the region of the reference plane A divided by the plan ROI (reference plane B) displayed on the display unit 12 based on the notified type of the reference plane B.

Specifically, at this time, the coordinate-system setting unit 16 narrows down the candidates of the type of the region based on the type of the already specified reference plane B, and instructs the main control unit 15 to display the candidates on the display unit 12. When the region coordinate system is to be defined, the direction of the coordinate axis (x-axis, y-axis, and z-axis) in a three-dimensional direction can be respectively determined according to the determined type of the region.

Specifically, when the reference plane B is the axial plane (YES at step S219), the coordinate-system setting unit 16 instructs the main control unit 15 to display "H/F (head/foot)" and "F/H (foot/head)" as the candidates of the type of the region to be divided (step S220).

When the reference plane B is not the axial plane (NO at step S219) but is the sagittal plane (YES at step S221), the coordinate-system setting unit 16 instructs the main control unit 15 to display "R/L (right/left)" and "L/R (left/right)" as the candidates of the region to be divided (step S222).

When the detected plane is not the axial plane nor the sagittal plane (when the plane is the coronal plane) (NO at step S221), the coordinate-system setting unit 16 instructs the main control unit 15 to display "A/P (anterior/posterior)" and "P/A (posterior/anterior)" as the candidates of the type of the region to be divided (step S223).

Upon receiving the type of the region selected from the displayed candidates via the input unit 11 (YES at step S224), the main control unit 15 notifies the coordinate-system setting unit 16 of the received type of the region.

Upon receiving of the type of the region, the coordinate-system setting unit 16 sets x-axis, y-axis, and z-axis based on the type of the region and the already specified reference planes A and B.

For example, when the axial plane is specified as the reference plane A, the sagittal plane is selected as the reference plane B, and the type of the region of the reference plane A to be divided by the plan ROI (reference plane B) is "L/R (left/right)", the coordinate-system setting unit 16 defines the z-axis vertically forward from back, the x-axis horizontally from left to right, and y-axis longitudinally upward from bottom, respectively, with respect to the reference plane A (step S225).

The coordinate-system setting unit 16 sets the region coordinate system by arranging such that the set x-axis, y-axis, and z-axis are respectively orthogonal to each other at the center of the plan ROI.

Because the process from step S226 to step S232 is the same as that from step S115 to step S121 shown in FIG. 5, explanations thereof will be omitted.

As explained above, in the second embodiment, the main control unit 15 receives operator's input of the type of the sectional image of any one of the axial plane, the sagittal plane, and the coronal plane via the input unit 11, and the coordinate-system setting unit 16 specifies the type of the sectional image, for which the input has been received, as the type of the reference plane A. The main control unit 15 receives operator's designation of the reference plane B orthogonal to the reference plane A via the input unit 11. When the designation of the reference plane B has been received, the coordinate-system setting unit 16 specifies the type of the reference plane B as any one of the axial plane, the sagittal plane, and the coronal plane. Further, the coordinate-system setting unit 16 specifies the vertical, horizontal, and anteroposterior directions in the reference plane A based on the types of the reference plane A and the reference plane B. Accordingly, the direction of the anatomical region can be flexibly defined according to the operator's judgment.

While exemplary embodiments of the present invention have been explained above, the invention is not limited thereto and can be carried out by various other embodiments.

For example, in the above embodiments, a case that the region coordinate system is set based on the operator's anatomical view has been explained. However, the region coordinate system can be automatically set based on the anatomical characteristic in the image obtained by scanning the object. In this case, the coordinate-system setting unit 16 detects the information of the shape (outline, length, and thickness) and the directions of the region from the image obtained by scanning the object, and specifies the directions of the axial plane, the sagittal plane, and the coronal plane based on the detected information, thereby setting the region coordinate system. Accordingly, the burden on the operator can be reduced.

In the above embodiments, a case that the coordinate-system setting unit 16 sets the region coordinate system for each region has been explained. However, for example, the same region coordinate system can be set for each object or scanning series with respect to a plurality of images stored in the storage unit 14. Accordingly, the direction is expressed based on the same standard with respect to a plurality of images obtained by scanning the object, or a plurality of images taken in the same scanning series. Therefore, diagnosis can be efficiently performed by using these images.

In the above embodiments, when the region coordinate system is set by the coordinate-system setting unit 16, the main control unit 15 calculates inclination (angle) of the region coordinate system with respect to the patient coordinate system, and when the calculated inclination exceeds a predetermined threshold, the main control unit 15 can display a warning on the display unit 12. Specifically, for example, there is no possibility that the head inclines a certain angle (for example, 45 degrees) or more with respect to a body axis, in view of a structure of a human body. Therefore, when the region coordinate system inclines the certain angle or more with respect to the patient coordinate system, the coordinate-system setting unit 16 displays the warning.

For a predetermined threshold used here, a plurality of angles can be set as the threshold. Accordingly, a different warning can be used for each threshold such that, for example, the degree of warning is changed based on the angle.

The region coordinate system cannot be inclined with respect to the patient coordinate system, basically, with regard to the chest and the abdomen of a patient. However, the region coordinate system can be inclined with respect to the patient coordinate system, with regard to internal organs such as a heart. In the above embodiments, because the reference plane is set by using a tomogram of the object, a specific coordinate system can be set with regard to the internal organs.

An MRI apparatus has been used above to explain some embodiments of the present invention. However, the present invention can be applied to other medical equipments such as X-ray CT scanners. An X-ray CT scanner is a device that collects the internal information of the object obtained by irradiating X rays to the object, and reconstructs the image by a computer based on the collected data.

Although one computer 10 has been shown in the drawings, the functions of the computer 10 can be distributed to a plurality of computers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical diagnostic imaging apparatus comprising:
a first digital data store region that stores therein a medical image of a patient;
a second digital data store region that stores therein information defining a relationship between a first coordinate system and at least one second coordinate system in association with the medical image, the first coordinate system being a patient coordinate system corresponding to a posture of the patient at a time of taking of the medical image, and the at least one second coordinate system being a regional coordinate system, different from the patient coordinate system, with its origin being located within a region of the medical image different from an origin of the patient coordinate system;
a display unit configured to display at least said region of the medical image; and
a control unit that causes the display unit to display the medical image region and direction information indicating a displayed direction of the region of the medical image based on stored information defining one of the coordinate systems.

2. The medical diagnostic imaging apparatus according to claim 1, further comprising:
a setting unit that sets the second coordinate system with respect to the medical image displayed on the display unit.

3. The medical diagnostic imaging apparatus according to claim 1, wherein the second digital data store region stores the relationship information in association with the medical image based on an anatomical characteristic in the region of the medical image containing the origin of the second coordinate system.

4. The medical diagnostic imaging apparatus according to claim 1, wherein the first digital data store region stores therein a plurality of medical images of the patient, and
the second digital data store region stores therein information defining a relationship between the first coordinate system and the second coordinate system that is identical for each patient or each scanning series, in association with the medical image.

5. The medical diagnostic imaging apparatus according to claim 1, further comprising:
a selecting unit configured to select which of the first coordinate system and the second coordinate system is used to define the displayed direction information.

6. The medical diagnostic imaging apparatus according to claim 1, further comprising a data transfer unit that transfers the medical image and information defining the second coordinate system associated with the medical image to an image processor.

7. The medical diagnostic imaging apparatus according to claim 1, further comprising a coordinate-system setting unit that sets a coordinate system associated with an anatomical characteristic of the patient as the second coordinate system, using a scanning plan image.

8. The medical diagnostic imaging apparatus according to claim 1, further comprising a coordinate-system setting unit that sets a coordinate system associated with an anatomical characteristic of the patient as the second coordinate system, based on information of a reference plane set with respect to an image obtained by scanning an oblique section of the patient or a scan planning image.

9. The medical diagnostic imaging apparatus according to claim 8, further comprising a data transfer unit that transfers the medical image and the information defining the second coordinate system associated with the medical image to an image processor.

10. The medical diagnostic imaging apparatus according to claim 8, further comprising:
a selecting unit that selects which of the first and second coordinate systems is used to define the displayed direction information.

11. A medical diagnostic imaging apparatus comprising:
a first storage unit that stores therein a medical image of an object;
a second storage unit that stores therein information about a relationship between a first coordinate system and a second coordinate system, information about the first coordinate system, and information of the second coordinate system, respectively, in association with the medical image, the first coordinate system corresponding to a posture of the object at a time of taking of the medical image, and the second coordinate system being different from the first coordinate system;
a display unit configured to display the medical image;
a control unit that causes the display unit to display the medical image and direction information indicating a direction of the medical image based on the information of the second coordinate system associated with the medical image;
a first designating unit that receives designation from an operator of a sectional image of a first region obtained by scanning an oblique section of a region of the object;
a first identifying unit that identifies a type of the sectional image of the first region as any one of an axial plane, a sagittal plane, and a coronal plane;
a third specifying unit that specifies vertical, horizontal, and anteroposterior directions in the sectional image of the first region; and
a setting unit that sets a coordinate system specific to each region as the second coordinate system, based on the type of the sectional image of the first region identified by the first identifying unit and each direction in the sectional image of the first region specified by the third specifying unit.

12. The medical diagnostic imaging apparatus according to claim 11, wherein the first identifying unit detects a plane having the smallest crossing angle with respect to the sectional image of the first region among an axial plane, a sagittal plane, and
a coronal plane in a patient coordinate system defined according to the posture and direction of the object, and identifies the type of the detected plane as the type of the sectional image of the first region.

13. The medical diagnostic imaging apparatus according to claim 11, wherein the first identifying unit receives an input of the type of at least one sectional image among an axial plane, a sagittal plane, and a coronal plane from an operator, and identifies the type of the sectional image, for which the input has been received, as the type of the sectional image of the first region.

14. The medical diagnostic imaging apparatus according to claim 11, further comprising:
a second designating unit that receives designation from the operator of a sectional image of a second region orthogonal to the sectional image of the first region; and
a second identifying unit that identifies a type of the sectional image of the second region as any one of an axial plane, a sagittal plane, and a coronal plane, wherein the third specifying unit specifies vertical, horizontal, and anteroposterior directions in the sectional image of the first region, based on the type of the sectional image of the first region identified by the first identifying unit and the type of the sectional image of the second region identified by the second identifying unit.

15. The medical diagnostic imaging apparatus according to claim 14, wherein the second identifying unit displays the types of two sectional images remaining after the type of the sectional image identified as the type of the sectional image of the first region is removed from the axial plane, the sagittal plane, and the coronal plane, and when either one of the displayed two sectional images is selected by the operator, the second identifying unit identifies the selected type of the sectional image as the type of the sectional image of the second region.

16. A computer implemented medical image processing method comprising:
   at least one computer processor programmed to perform the following:
   storing a medical image of a patient;
   storing information defining a relationship between a first coordinate system and at least one second coordinate system in association with the medical image, the first coordinate system being a patient coordinate system corresponding to a posture of the patient at a time of taking of the medical image, and the at least one second coordinate system being a regional coordinate system, different from the patient coordinate system, with its origin being located within a region of the medical image different from an origin of the patient coordinate system;
   displaying at least a region of the medical image; and
   controlling the display unit to display the medical image region and to also display direction information indicating a displayed direction of the region of the medical image based on stored information defining one of the coordinate systems.

17. A computer program product having a tangible computer readable medium including non-transitory programmed instructions for processing a medical image, wherein the instructions, when executed by a computer, cause the computer to perform:
   storing a medical image of a patient;
   storing information defining a relationship between a first coordinate system and at least one second coordinate system in association with the medical image, the first coordinate system being a patient coordinate system corresponding to a posture of the patient at a time of taking of the medical image, and the at least one second coordinate system being a regional coordinate system, different from the patient coordinate system, with its origin being located within a region of the medical image different from an origin of the patient coordinate system;
   displaying at least a region of the medical image; and
   controlling the display unit to display the medical image region and to also display direction information indicating a displayed direction of the region of the medical image based on stored information defining one of the coordinate systems.

* * * * *